(12) United States Patent
Rubin et al.

(10) Patent No.: US 7,442,818 B2
(45) Date of Patent: Oct. 28, 2008

(54) METHOD OF MAKING ESTERS AND CATALYSTS THEREFORE

(76) Inventors: David Rubin, 8949 Montrose Way, San Diego, CA (US) 92122; Eyal Rubin, 8949 Montrose Way, San Diego, CA (US) 92122

( * ) Notice: Subject to any disclaimer, the term of this patent is extended or adjusted under 35 U.S.C. 154(b) by 240 days.

(21) Appl. No.: 11/373,994

(22) Filed: Mar. 14, 2006

(65) Prior Publication Data
US 2007/0219384 A1    Sep. 20, 2007

(51) Int. Cl.
*C11C 1/00*  (2006.01)

(52) U.S. Cl. .................................................... 554/167

(58) Field of Classification Search .................. None
See application file for complete search history.

(56) References Cited

U.S. PATENT DOCUMENTS

| | | |
|---|---|---|
| 4,348,399 A | 9/1982 | Shepherd |
| 5,831,115 A | 11/1998 | Arendsen et al. |
| 5,965,614 A | 10/1999 | Audia et al. |
| 6,399,628 B1 | 6/2002 | Audia et al. |
| 6,630,600 B1 | 10/2003 | Andersson et al. |
| 6,916,850 B2 | 7/2005 | Wang et al. |
| 2003/0013657 A1 | 1/2003 | Wang et al. |
| 2003/0013847 A1 | 1/2003 | Wang et al. |
| 2004/0058937 A1 | 3/2004 | Aitken et al. |

OTHER PUBLICATIONS

Janout et al., Chem. Abstr. of "Polymer regaents:preparation ofpolymer esters.thiocarboxylic acids absed on crosslinked polystrene", Inst. Macromol. Chem. Czech. Acad. Sci., 1986.*

* cited by examiner

*Primary Examiner*—Deborah D Carr
(74) *Attorney, Agent, or Firm*—Browdy and Neimark, P.L.L.C.

(57) ABSTRACT

Esters of organic acids are produced by a transesterification reaction by reacting a first ester with an alcohol to form a second ester in the presence of a catalyst comprising a mixture of DCC and DMAP.

10 Claims, No Drawings

METHOD OF MAKING ESTERS AND CATALYSTS THEREFORE

FIELD OF THE INVENTION

The present invention relates to a method for making ester of organic acids and catalysts for use in this method.

BACKGROUND OF THE INVENTION

Esters of organic acids are commercially extremely useful for a variety of purposes. Lower esters are extensively used as solvents in coatings, inks and adhesives, and in processing other substances. They readily dissolve resins or their precursors to become vehicles for application of coatings, etc.

Esters are also widely used as plasticizers in polymers. These esters include the benzoates, phthalates, terephthalates, and trimetillates, and aliphatic dibasic acid esters. Varying the acid or the alcohol components modifies the efficacy of the resultant ester as a plasticizer. For example, phthalate plasticizers, the molecular sizes of the alcohol moiety can be varied from methyl to tridecyl to control permanence, compatibility, and efficiency; branched (e.g., 2-ethylhexyl, isodecyl) for rapid absorption and fusion, or linear ($C_6$-$C_{11}$) for low temperature flexibility.

Unsaturated and difunctional ester are important monomers for the manufacture of many commercial polymers. For example, polymerization of vinyl acetate and methyl methacrylate produces poly(vinyl acetate) and methyl methacrylate. Another example is dimethyl terephthalate, which reacts with ethylene glycol to yield poly)ethylene terephthalate).

Monohydric alcohol esters of dibasic acids and polyol esters of monobasic acids are used as synthetic lubricants. They are generally prepared from $C_8$-$C_{13}$ monohydric alcohols, polymethylol compounds such are trimethylolpropanes, pentaerythritol, and dipentaerythritol; $C_6$-$C_{10}$ monobasic acids such as heptanoic and nonanoic acids, and $C_6$-$C_{10}$ dibasic acids such as adipic, azelaic and sebacic acids, and phthalic anhydride. These esters are mainly used as base oils in high performance lubricants for engines and machinery.

Esters in the form of fats and oils from tallow and plants such as soybean, cottonseed, linseed and castor bean are important raw materials for soap, paints and food industries.

Polyol (e.g., glycerol, sorbitol, sucrose and propylene glycol or poly(ethylene oxide) esters of long-chain fatty acids are nonionic surfactants used in foods, pharmaceuticals, cosmetics, textiles, cleaning compounds, and many other applications.

Many esters are used as pharmaceuticals. Of these, benzocaine, ethyl 4-aminobenzoate, is a topical anesthetic. Phenyl salicylate has antipyretic, antirheumatic, and antiparasitic properties. Some simple benzoates are also used as antiseptic agents. Salicylic acid esters are used as antibacterial agents and pain relievers. Analgesic balms, creams, sprays, and nasal inhalers usually contain various combinations of either methyl or menthyl salicylate and menthol.

In general, esterification of a physiologically active alcohol or phenol with aliphatic carboxylic acid or an acid with alcohol detoxifies it by decreasing the concentration of thee active component present. The active compound is released gradually in the body by hydrolysis of the ester. Examples of these include aspirin, a common analgesic; methyl phenidate, a central nervous system stimulate; and clofibrate, an antihyperlipoproteinemic.

Many parent drugs have been converted to esters to generate so-called prodrugs in order to overcome some undesirable property, such as bitter taste, poor absorption, poor solubility, and irritation and injection site. For example, antibiotics such as chloramphenicol and clindamycin have been derivatized as their palmitate esters in order to minimize their bitter taste. In order to improve the poor oral absorption of carbencillin, a lipophilic indanyl ester has been produced. Prednisolone, a steroid, is derivatized to its $C_{21}$ hemisuccinate sodium salt to make it extremely water-soluble.

Several esters are used as herbicides and pesticides. Many halogenated benzoic acid esters are phytotoxic and are used as herbicides. Demthyltetrachloroterephthalate and diisopropyl 5-nitroisophthalate are used as herbicide and fungicide, respectively. The phenoxy herbicides are primarily propyl, butyl and isooctyl esters of 2, 4-dichlorophenoxyacetic acid, 4-chloro-2-methylphenoxyacetic acid, and methyl, ethyl or butyl esters of 2-(4-hydroxyphenoxy)propionic acid. Because of their low toxicity, high selectivity, and relatively short life in the soil, phenoxy herbicides are widely used. They are used for controlling weeds in a large number of grass crops such as corn, small grains, sorghum, rice, sugarcane, pasture, range land and turf.

Pyrethroids are synthetic esters produced to imitate or improve the activity of biological principals of the pyrethrum plant. They are powerful contact insecticides, causing rapid knockdown of treated insects. The pyrethroids are extensively used in controlling insect pests on fruit trees, vegetables, and other field crops in space sprays and contact sprays to kill insects infesting homes, industrial locations, and nonfood processing areas; and in protection of warehoused food. These compounds include fenvelerate, flucythrinate, allethrin, cyfluthrin, deltamethrin, permethrin, and tetramethrin.

Since esters can be easily hydrolyzed, they are used as protecting groups for hydroxyl and carboxylic acid groups. Acetates and benzoates are widely used in carbohydrate, steroid and nucleoside chemistry, and their cleavage is based on hydrolysis with base, ammonolysis, or methanolysis. Of great importance in peptide chemistry are the t-butyl, benzyl, and substituted benzyl esters.

Esters are conventionally produced by reacting an alcohol with an organic acid in the presence of a catalyst, or by transesterification of an ester in which the alcohol group of the ester is replaced by another alcohol group.

One example of such transesterification is the preparation of ethyl esters of fatty acids from triglycerides. In this process, a triglyceride is mixed with absolute ethanol and catalytic amounts of sodium or potassium methoxide. The mixture is then left for at least twelve hours, or overnight, and then washed with water to remove the glycerin, ethanol, and sodium or potassium methoxide.

One widely used catalyst for preparation of esters is 4-dimethylaminopyridine (DMAP). This catalyst can be used for acid-alcohol reactions or for transesterification reactions. However, the reaction times are measured in hours.

SUMMARY OF THE INVENTION

It is an object of the present invention to overcome the aforesaid deficiencies in the prior art.

It is another object of the present invention to prepare esters from alcohols and acids.

It is a further object of the present invention to prepare esters by transesterification.

It is still another object of the present invention to provide a catalyst for preparing esters, either by acid-alcohol reaction or by transesterification.

It is another object of the present invention to prepare esters of fatty acids from triglycerides of the acids.

Esters of organic acids can be produced using a catalyst comprising a combination of 2,3-dichlorohexylcarbodiimide (DCC) and 4-dimethylaminopyridine (DMAP). This catalyst composition makes it possible to prepare and ester of an organic acid either by a transesterification within minutes rather than hours, and the reaction is conducted at or below room temperature, preferably about 0-5° C. This remarkable shortening of the time required to produce esters using the catalyst of the present invention is critical in mass production of esters, as a factory can increase is production many time folds for a given batch of ester. Another advantage of the process of the present invention is that the reaction takes place at room temperature or lower, thereby significantly reducing production costs related to the heating and handling of hot materials, as well as reducing decomposition of the materials used in the reaction.

While the catalyst composition of the present invention is suitable for use in preparing esters of organic acids by transesterification, the catalyst composition is particularly well suited to preparing lower alkyl esters of fatty acids from triglycerides of the fatty acids. One specific example of this is preparation of ethyl esters of fatty acids from triglycerides derived, for example, from fish oil. These esters reduce the "fishy" smell of fish oils.

Fish oil contains omega-3 fatty acids, which are not stable at temperatures much above room temperature. The transesterification of triglycerides of fish oil fatty acids according to the present invention avoids the problem of the heat sensitivity of these compounds, as reaction below room temperature is preferred.

DETAILED DESCRIPTION OF THE INVENTION

Catalytic amounts of a combination of DCC and DMAP are added to a transesterification reaction. This catalyst drives the reaction to completion in a matter of minutes, generally about one to about ten minutes. The reaction occurs at room temperature or, preferably, below room temperature. The combination of DCC and DMAP can be used in proportions ranging from about 100:1 to 1:100 by weight. (DCC:DMAP)

This catalyst composition can be used for preparation of any type of esters by a transesterification of the original ester reaction. The only limitation is steric hindrance of the acid group and the alcohol group used to produce the new ester.

Basically, the reaction is the following:

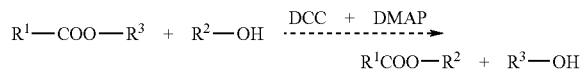

In this reaction, $R^1$, $R^2$ and $R^3$ are individually selected from the group consisting of substituted or unsubstituted alkyl, alkenyl, alkynyl carbon chains, substituted or unsubstituted cyclic groups, substituted or unsubstituted aryl groups, substituted or unsubstituted cyloalkyl groups, or substituted or unsubstituted heteroaryl groups.

The reaction does not occur in water alone, but can be conducted in oil or any conventional solvent such as dichloromethane, dimethylformamide (DMF) or DMSO. There are substantially no side reactions, so there is no problem of disposing of unwanted products of the reaction. The reaction is not conducted in water or an aqueous liquid because DCC absorbs water very strongly, and its bonds are opened in the presence of water.

The reaction is conducted at room temperature or, preferably, below room temperature. Preferred temperatures for conducting the reaction are about −5° C. to about 15° C., and more preferred, about 0° C. to about 5° C.

As used herein, alkyl, alkenyl and alkynyl carbon chains, if not specified otherwise, contain from about 1 to about 20 carbon atoms, preferably from about 1 to about 16 carbon atoms, and are straight or branched. Alkenyl carbon chains of from about 1 to about 20 carbon atoms preferably contain from about 1 to about 8 double bonds; the alkenyl carbon chains of about 1 to about 16 carbon atoms preferably contain from about 1 to about 5 double bonds.

Alkynyl carbon chains of from about 1 to about 20 carbon atoms preferably contain from about 1 to about 8 triple bonds, and the alkynyl carbon chains of about 1 to about 16 carbon atoms preferably contain about 1 to about 5 triple bonds.

The alkyl, alkenyl and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms. The alkyl group substituent includes halos, haloalkyl, preferably halo lower alkyl, aryl, hydroxyl, alkoxy, aryloxy, alkoxy, alkylthio, arylthio, aralkoxy, aralkylthio, carboxy, alkoxycarbonyl, oxo and cycloalkyl.

For the present invention, "cyclic" refers to cyclic groups preferably contains from about 3 to about 19 carbon atoms, preferably 3 to 10 carbon atoms, and more preferably 5 to 7 carbon atoms. Cyclic groups include heteroatoms, and may include bridged rings or fused rings, either heterocyclic, cyclic, or aryl.

The term "aryl" herein refers to aromatic cyclic compounds having up to about 10 atoms, including carbon atoms, oxygen atoms, sulfur atoms, selenium atoms, etc. Aryl groups include, but are not limited to, groups such as substituted and unsubstituted phenyl, substituted or unsubstituted naphthyl, and substituted or unsubstituted fused ring systems having aromatic unsaturation. The fused ring system can contain up to about seven rings.

An "aryl group substituent" as used herein includes, alkyl, cycloalkyl, cycloaryl, aryl, heteroaryl, optionally substituted with one or more, preferably 1 to 3, substituents selected from halo, haloalkyl, alkyl, arylalkyl, heteroarylalkyl, alkenyl containing 1 to 2 double bonds, alkynyl containing 1 to 2 triple bonds, halo, hydroxyl, polyhaloalkyl, preferably trifluoromethyl, formyl, alkylcarbonyl, arylcarbonyl, optionally substituted with 1 to 3 substituents selected from halo, haloalkyl, alkyl, heteroayrlcarboxyl, carboxyl, alkoxycarbonyl, aryloxycarbonyl, aminocarbonyl, alkylaminocarbonyl, dialkylaminocarbonyl, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothicyano, alkylsulfinyl, alkylsulfonyl, arylsulfinyl, arylsulfonyl, aminosulfonyl, alkylaminosulfinyl, dialkylaminosulfonyl, and arylaminosulfonyl.

The term "arylalkyl" is used herein refers to an alkyl group which is substituted with one or more aryl groups. Examples of arylalkyl groups include but are not limited to benzyl, 9-fluorenylmethyl, naphthylmethyl, diphenylmethyl, and triphenylmethyl.

"Cycloalkyl" as used herein refers to a saturated mono- or muticyclic ring system, preferably of about 3 to about 10 carbon atoms per ring, more preferably of 3 top 6 carbon atoms per ring. Cycloalkenyl and cycloalklynyl refer to mono- or multicyclic ring systems that respectively include at least one double bond and at least one triple bond. Cycloalkenyl and cycloalkynyl groups may preferably contain about 3 to about 10 carbon atoms, with cyclylo groups more preferably contains 4 to 7 carbon atoms and clyclclkynyl groups more preferably contain 8 to 10 carbon atoms. The ring systems of the cycloalkyl, cycloalkenyl and cycloalkynyl groups may be composed of one ring or of two or more rings which may be joined together in a fused, bridged, or spiro-connected fashion, and may be optionally substituted with one or more alkyl group substituents.

The term "heteroaryl" for purposes of the present application refers to a monocyclic or multicyclic ring system. Preferably with about 5 to about 15 ring members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3 m, aryl group substituents. Exemplary heteroaryl groups include, for example, furanyl, thienyl, pyridyl, pyrrolyl, N-methylpyrrolyl, quinolinyl, and isoquinolinyl.

The term "heterocyclic" refers to a monocyclic or multicyclic ring system, preferably of 3 to ten rings, more preferably 4 to 7 rings, where one or more, preferably 1 to 3, of the atoms in the ring system is a heteroatom, i.e., an atom that is other than carbon, such as nitrogen, oxygen, or sulfur. The heterocycle may be substituted optionally with one or more, preferably 1 to 3, aryl group substituents. Preferred substituents on the heterocyclic group include hydroxyl, alkoxy, halo and lower alkyl. The term "heterocyclic" may include heteroaryl. Exemplary heterocyclics include, for example, pyrrolidinyl, piperidinyl, alkylpiperidinyls, morpholinyl, oxadiazolyl, or triazolyl.

The nomenclature alkyl, carbonyl, etc., is used as is generally understood by those of skill in this art. As used herein, alkyl refers to saturated carbon chains that contain one or more carbon chains. The chains may be straight or branched on include cyclic portions or may be entirely cyclic.

The terms "halogen", "halo" or "halide" includes fluorine, chlorine, bromine, and iodine. This can include pseudohalides, which are anions that behave substantially similarly to halides. These compounds can be used in the same manner and treated in the same manner as halides. Pseudohalides include, but are not limited to, cyamide, cyanate, thiocyanate, selenocyanate, trifluoromethyl, and azide. The term "haloalkyl" refers to a lower alkyl radical in which one or more of the hydrogen atoms are replaced by halogen, including but not limited to chloromethyl, trifluoromethyl, 1-chloro-2-fluoroethyl, and the like.

"Haloalkoxy" refers to RO— in which R is a haloalkyl group.

The term "sulfinyl" refers to —S(O)—. "Sulfonyl" refers to —S(O)$_2$—.

"Aminocarbonyl" refers to —C(O)NH$_2$.

"Alkylene" refers to a straight, branched, or cyclic, preferably straight or branched, bivalent aliphatic hydrocarbon group, preferably having form 1 to about 20 carbon atoms. The alkylene group is optionally substituted with one or more alkyl group substituents. The may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to about 6 carbon atoms. Preferred alkylene groups are lower alkylene, with alkylene of 1 to 3 atoms particularly preferred.

The term "alkenylene" as used herein refers to a straight, branched or cyclic, preferably straight of branched, bivalent aliphatic hydrocarbon group, preferably having from about 1 to about 20 carbon atoms and at least one double bond. The alkenylene group is optionally substituted with one or more alkyl group substituents. There maybe optionally inserted along the alkenylene group one or more oxygen, sulfur, or substituted or unsubstituted nitrogen atoms, wherein the nitrogen substituent is alkyl, as previously described.

As used herein, "alkynylene" refers to a straight, branched or cyclic bivalent aliphatic hydrocarbon group having from about 1 to about 20 carbon atoms and at least one triple bond. The alkynylene group is optionally substituted with one or more alkyl group substituents. There may be optionally inserted along the alkynylene group one or more oxygen, sulfur, or substituted or unsubstituted nitrogen atoms, where the nitrogen substituent is alkyl. The term "lower alkynylene" refers to alkynylene groups having from 2 to 6 carbon atoms.

The term "arylene" as used herein refers to a monocyclic or polycyclic bivalent aromatic group preferably having from about 1 to about 20 carbon atoms and at least one aromatic ring. The arylene group is optionally substituted with one or more alkyl group substituents. There may be optionally inserted around the arylene group one or more oxygen, sulfur, or substituted or unsubstituted nitrogen atoms, where the nitrogen substituent is alkyl.

"Heteroarylene" refers to a bivalent monocyclic or multicyclic ring system, preferably of about 5 to about 15 rings, wherein one or more of the atoms in the ring system is a heteroatom. The heteroarylene may be optionally substitute with one or more aryl group substituents.

The term "alkylidene" refers to a bivalent group, such as =CR'R", which is attached to one atom of another group, forming a double bond.

"Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

EXAMPLES

The following non-limiting examples are provided solely for the purpose of illustrating particular embodiments of the invention and are not intended to limit the scope of the specification, including the claims, in any manner.

Example 1

One gram of NaOH was dissolved in 200 mL dry ethanol in a two-liter flask. One hundred mg of DCC and 50 mg of DMAP were added. When the solution became clear (after 1-2 minutes), 500 grams of fish oil was added. The mixture was stirred for two minutes, and then left to rest for another three to five minutes without agitation. Next, the mixture washed with five liters of tap water three times in a separating funnel. The solution was then dried over MgSO$_4$ and filtered.

The glycerin released during this reaction was recovered by leaving the mixture for an additional two hours to allow the glycerin to separate or, alternatively, after the five minutes of reaction time, rather than two hours of waiting, the mixture can be centrifuged for 5-10 minutes at about 2000 RPM to recover glycerin.

Thus, the expressions "means to . . . " and means for . . . " as may be found in the specification above and/or in the claims below, followed by a functional statement, are intended to define and cover whatever structural, physical, chemical, or electrical, element or structures which may now or in the future exist for carrying out the recited function, whether or nor precisely equivalent to the embodiment or embodiments disclosed in the specification above. It is intended that such expressions be given their broadest interpretation.

What is claimed is:

1. A method for making organic esters by transesterification comprising reacting a first ester with an alcohol in the presence of a catalyst comprising a mixture of DMAP and DCC to produce a second ester.

2. The method according to claim 1 wherein the reaction is conducted at a temperature of from about −5° C. to about 15° C.

3. The method according to claim 2 wherein the reaction is conducted at a temperature of from about 0° C. to about 5° C.

4. The method according to claim 1 wherein the reaction is conducted in a solvent selected from the group consisting of DMSO, DMF and dichloromethane.

5. The method according to claim 1 wherein the ester is a triglyceride of fish oil fatty acids.

6. The method according to claim 5 wherein the alcohol is ethanol.

7. The method according to claim 5 wherein glycerin released from the triglyceride is obtained by leaving the reaction mixture for about two hours to allow the glycerin to separate.

8. The method according to claim 5 wherein glycerin released from the triglyceride is obtained by centrifuging the mixture for about five to ten minutes at about 2000 RPM.

9. A method for making organic esters by transesterification comprising reacting a first ester with an alcohol in the presence of a catalyst comprising a mixture of DMC and DMAP to produce a second ester;
wherein the reaction is

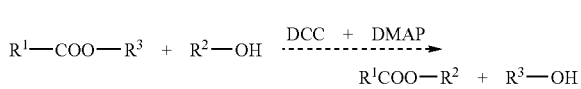

and $R^1$, $R^2$ and $R^3$ are individually selected from the group consisting of substituted or unsubstituted alkyl, alkenyl or alkynyl carbon chains; substituted or unsubstituted cyclic groups; substituted or unsubstituted aryl groups; substituted or unsubstituted cyloalkyl groups; and substituted or unsubstituted heteroaryl groups.

10. The method according to claim 1 wherein the combination of DCC and DMAP is in a proportion ranging from about 100:1 to 1:100 by weight of DCC:DMAP.

* * * * *